(12) United States Patent
Choudhary et al.

(10) Patent No.: US 9,381,182 B2
(45) Date of Patent: Jul. 5, 2016

(54) ANTHRANILIC ACID DERIVATIVES: NOVEL INHIBITORS OF ADVANCED GLYCATION END-PRODUCTS (AGES) FORMATION

(71) Applicants: Muhammad Iqbal Choudhary, Karachi (PK); Humera Jahan, Karachi (PK); Kahlid Mohammed Khan, Karachi (PK); Amber Atta, Karachi (PK); Atta-ur- Rahman, Karachi (PK)

(72) Inventors: Muhammad Iqbal Choudhary, Karachi (PK); Humera Jahan, Karachi (PK); Kahlid Mohammed Khan, Karachi (PK); Amber Atta, Karachi (PK); Atta-ur- Rahman, Karachi (PK)

( * ) Notice: Subject to any disclaimer, the term of this patent is extended or adjusted under 35 U.S.C. 154(b) by 337 days.

(21) Appl. No.: 13/968,071

(22) Filed: Aug. 15, 2013

(65) Prior Publication Data

US 2015/0051286 A1    Feb. 19, 2015

(51) Int. Cl.
*A61K 31/196*    (2006.01)

(52) U.S. Cl.
CPC ................................. *A61K 31/196* (2013.01)

(58) Field of Classification Search
CPC .................................................... A61K 31/196
See application file for complete search history.

(56) References Cited

U.S. PATENT DOCUMENTS

2010/0029613 A1*  2/2010  Nedergaard ......... A61K 31/553
                                                                   514/212.01

* cited by examiner

*Primary Examiner* — Yong Chong
(74) *Attorney, Agent, or Firm* — Sarfaraz K. Niazi

(57) ABSTRACT

Anthranilic acid derivatives are used to inhibit the formation of advanced glycation end products to reduce complications in diabetes.

1 Claim, 3 Drawing Sheets

ANTHRANILIC ACID DERIVATIVES: NOVEL INHIBITORS OF ADVANCED GLYCATION END-PRODUCTS (AGES) FORMATION

BACKGROUND OF THE INVENTION

The General Assembly of United Nations unanimously passed the resolution 61/225 to declare that diabetes as a global health concern and one of the major health challenges of the 21$^{St}$ century. According to the International Diabetes Federation (IDF) and the Baker IDI Heart, currently 285 million people are affected by this debilitating disease, and the figure will be projected to be 438 million by 2030. Until now, genetic predisposition and behavioral and environmental factors were considered as potential contributors, but recently epigenetic influences, such as the impact of in-utero effects and the maternal milieu, particularly in type II diabetes have been recognized as equally important risk factors. Therefore, coordinated efforts have been made in the west for the prevention and treatment of the disease (Zimmet P Z, et al., 2011).

Diabetes mellitus is characterized by elevated blood sugar levels. Hyperglycemia is the significant factor in causing non-enzymatic glycation of amino groups of body proteins, which lead to the formation of irreversible, reactive advanced glycation end-products (AGEs). The Maillard reaction or non-enzymatic glycation of proteins was initially identified by a French scientist, Louis Maillard in 1912. The reaction was initially investigated in food stuff, as heating, processing and storage and is associated with a variety of food-related phenomena, such as color, flavor and aroma. The reaction was later investigated in diabetic individuals after the discovery of glycated hemoglobin (HbA1c). Therefore, the Maillard reaction is analyzed in many fields due to its chemical, toxicological and pathophysiological properties (Wu C H, et al., 2011; Peyrous J, et al., 2006).

The Maillard reaction is a complex cascade of reaction and follows the similar pattern of free-radical chain reaction (Wu C H, et al., 2011). It is generally comprised of three stages:

Initiation Reaction: The carbonyl group of reducing sugars, such as glucose, fructose and ribose reacts non-enzymatically with the free amino groups of peptides, proteins, nucleic acid and lipids to form Schiff base, which is followed by a relatively stable product recognized as an Amadori product or ketoamine. The reaction equilibrium is greatly dependent on concentration of the initiation substrate and the duration of exposure, therefore the reaction is reversible till the formation of Amadori product (Peyrous J, et al., 2006).

Propagation Reaction: The ketoamine (Amadori product) either regenerates amines via metal ion-induced catalysis and oxygen-mediated oxidation or interacts with the amino acids, which results in the formation of carboxymethyl lysine (CML), while the dehydration of glycosyl group leads to the formation of highly reactive carbonyl intermediate 3-deoxyglucosone (DG) (Wu C H, et al., 2011).

Advanced Stage: The reactive carbonyl intermediate 3-DG interacts with the lysine residue of proteins, which results in the formation of pyrraline, an advanced glycation end-product (AGE). The stage also involves the reaction between pentose and lysine and arginine residues of proteins to form pentosidine (AGE) or other adducts. As a consequence, intra- and intermolecular cross-linking of proteins and fragmentation processes occur, which lead to the irreversible protein damages and denaturation. Besides these, other types of AGEs, which are also derived from the intermediate stage of the Maillard reaction, have been identified, including glyoxal-lysine dimer (GOLD), methylglyoxal-lysine dimer (MOLD), carboxyethyl-lysine dimer (CEL). These AGEs are highly heat stable and constitute the ultimate stage of the Maillard reaction (Wu C H, et al., 2011).

AGEs have been involved in the pathophysiology of many late complications of diabetes, such as diabetic micro- and macro vascular complications, including neuropathy, nephropathy, retinopathy and peripheral vascular diseases, stroke and myocardial infarction (Gutierrez R M P, et al., 2010). Although the mechanism involved in the pathogenesis of diabetic late complications is not completely understood, but many features have been examined, such as protein glycation results in the formation and accumulation of tissue AGEs, and hence irreversibly alter the structural and functional chemistry of affected proteins; the interaction of AGEs with their receptors known as RAGE (receptors for advanced glycation end-products) which are expressed on many cell types and up-regulated under hyperglycemic conditions, results in the generation of intracellular oxidative stress and induction of many proinflammatory cytokines, which lead to intracellular derangements in biological systems (Wu C H, et al., 2011).

The first identified AGEs inhibitor, aminoguanidine is a synthetic small hydrazine analog, has shown inhibitory potential in the formation of AGEs and has been used in phase III clinical trials for the treatment of diabetic nephropathy. Unfortunately, the trail has been terminated because of its undesirable side effects, such as gastrointestinal disorders, anemia and flu-like symptoms (Adisakwattana S, et al., 2012). These side effects perhaps due to the sequestration of pyridoxal group, which lead to the deficiency of vitamin $B_6$ (Gutierrez R M P, et al., 2010).

BRIEF SUMMARY OF THE INVENTION

Many studies have highlighted the contribution of AGEs in disease states and primarily investigated their deleterious effects and their possible mechanism of actions. Therefore, there is a need of synthesis and investigation of novel antiglycation agents, which are devoid of any adverse effects, may present a therapeutic approach for the delaying and treatment of premature aging and vascular abnormalities in diabetic patients. In the current study, we explored the novel antiglycation agents (1-18), which are potent inhibitors against the glycation process, and belong to anthranilic acid derivatives. The inhibitors were identified by using high throughput screening method, fluorescence-based antiglycation assay (see Table-1). The cytotoxicity studies were performed against mouse fibroblast cell-line (3T3 Cell-line) by employing MTT-based cytotoxicity assay. The mechanistic studies were also conducted to evaluate the effect of novel antiglycation inhibitors on AGEs-induced intracellular reactive oxygen species generation (ROS) and associated impaired proliferation in rat hepatocytes via dichlorofluorescin diacetate (DCFH-DA) and MTT-based cytotoxicity assay, respectively. Previously, these novel antiglycation inhibitors were known for anticancer and anti-inflammatory activities (Congiu C, et al., 2005).

TABLE 1

| Compound | Antiglycation Activity | | Cytotoxicity % Inhibition |
|---|---|---|---|
| | % Inhibition | $IC_{50} \pm$ SEM [μM] | |
| 2-(2,4-Dinitroanilino) benzoic acid (1) | 90% | 67.2 ± 0.004 | 1.5% |
| 2-(4-Chloro-2-nitroanilino) benzoic acid (2) | 82% | 137 ± 0.002 | 5.6% |

TABLE 1-continued

| Compound | Antiglycation Activity | | Cytotoxicity % Inhibition |
|---|---|---|---|
| | % Inhibition | $IC_{50} \pm$ SEM [μM] | |
| 2-(5-Chloro-2,4-dimethoxyanilino) benzoic acid (3) | 75.1% | 266 ± 0.016 | 22.4% |
| 2-(4-Chloro-3-nitroanilino) benzoic acid (4) | 68.9% | 266 ± 0.010 | 19.7% |
| 2-(4-Chloroanilino) benzoic acid (5) | 62% | 298 ± 0.015 | 41.3% |
| 2-(2-Chloroanilino) benzoic acid (6) | 68% | 426 ± 0.017 | 0.9% |
| 2-(3-Chloro-5-nitroanilino) benzoic acid (7) | 84.4% | 166 ± 0.017 | 13.0% |
| 2-(5-Chloro-2-methylanilino) benzoic acid (8) | 69% | 408 ± 0.03 | 3.2% |
| 2-(2-Chloro-5-nitroanilino) benzoic acid (9) | 79.4% | 314 ± 0.010 | 3.0% |
| 2-(2,4-Difluoroanilino) benzoic acid (10) | 63% | 558 ± 0.066 | 1.1% |
| 2-(3,4-Dichloroanilino) benzoic acid (11) | 62% | 597 ± 0.021 | 40.1% |
| 2-(4-Butylanilino) benzoic acid (12) | 70% | 407 ± 0.01 | 17.3% |
| 2-(3,5-Dimethylanilino) benzoic acid (13) | 65% | 457 ± 0.019 | 4.8% |
| 2-(2,5-Dichloro-4-nitroanilino) benzoic acid (14) | 88.8% | 84.8 ± 0.003 | 29.6% |
| 2-(2,5-Dichloroanilino) benzoic acid (15) | 62% | 678 ± 0.047 | 1.6% |
| 2-(3-Nitroanilino) benzoic acid (16) | 80% | 264 ± 0.013 | 4.1% |
| 2-(5-Chloro-2-nitroanilino) benzoic acid (17) | 78% | 150 ± 0.001 | 1.5% |
| 2-(3-Methoxyanilino) benzoic acid (18) | 71% | 398 ± 0.007 | 7.1% |

DETAILED DESCRIPTION OF THE INVENTION

Figure 1:
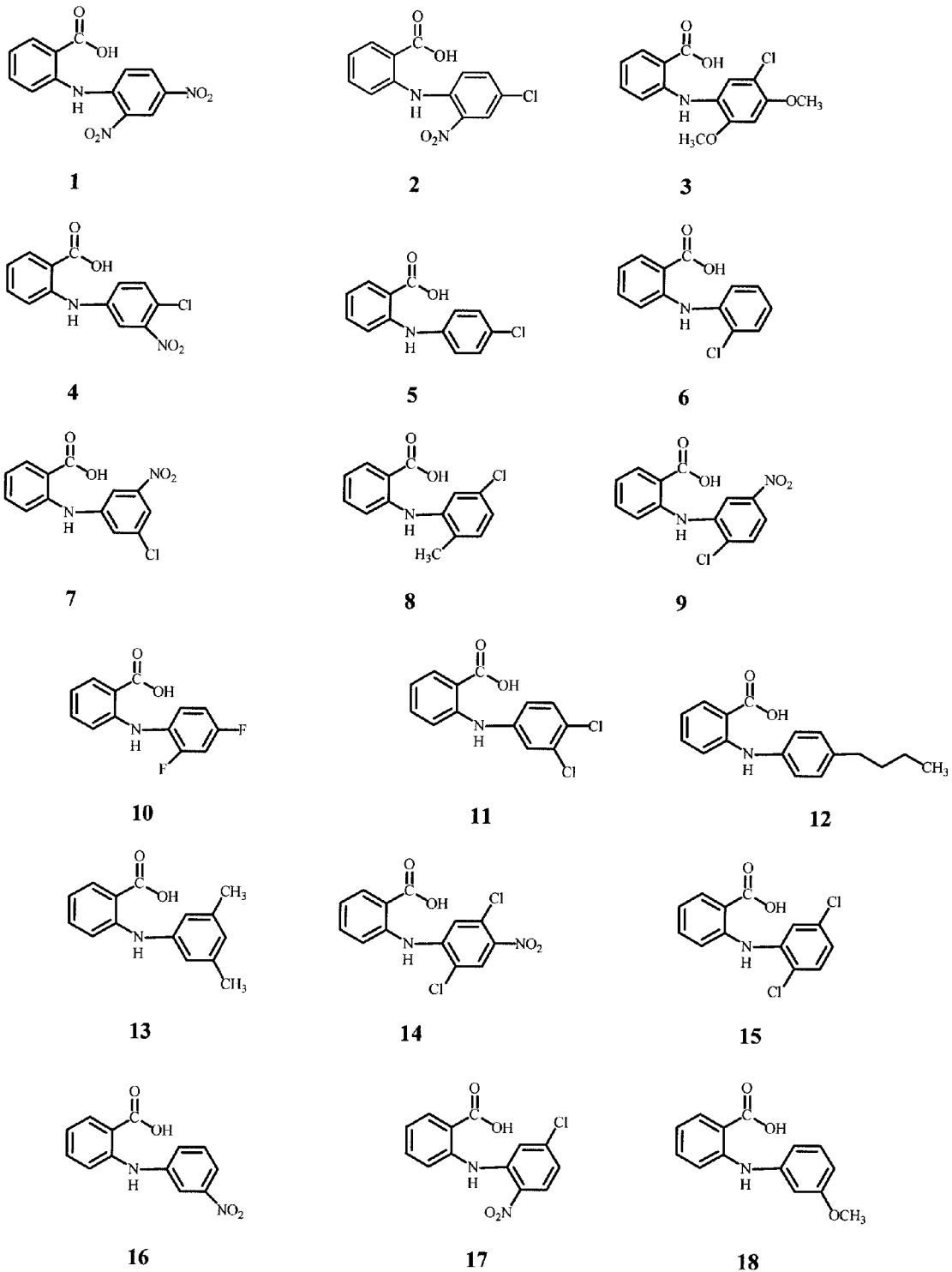
FIG. 1 depicts the structures of novel identified antiglycation agents, anthranilic acid derivatives.
Figure 2A:
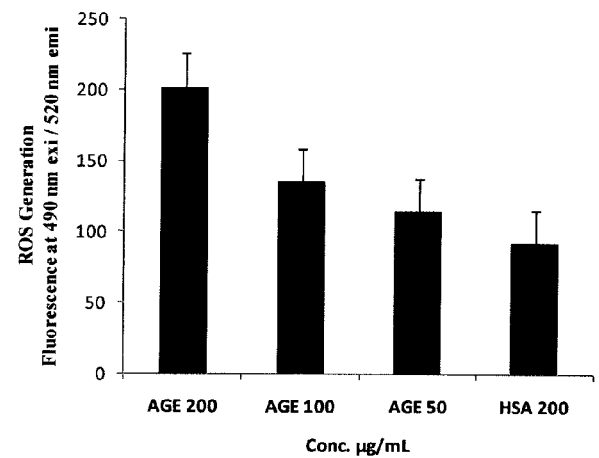
FIG. 2A depicts the fructose-derived AGE mediated ROS production in rat hepatocytes. The hepatocytes were treated with the probe, DCFH-DA first and then incubated with the specified concentrations of AGEs for 24 hours at 37° C. The indicated ROS values are the mean of two independent experiments.
Figure 2B:
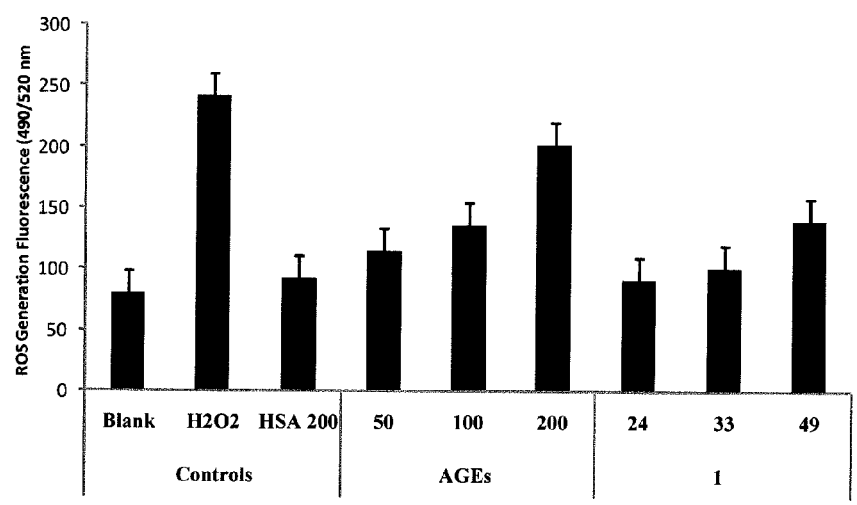
FIG. 2B depicts the effect of novel identified antiglycation agent, compound 1 on AGE-mediated ROS production in rat hepatocytes. The hepatocytes were pre-treated with DCFH-DA for 45 mins at 37° C. and then treated with the specified concentrations of compound 1, incubated with the AGEs (200 μg/mL) for 24 hours at 37° C. The indicated ROS values are the mean of two independent experiments.
Figure 3:
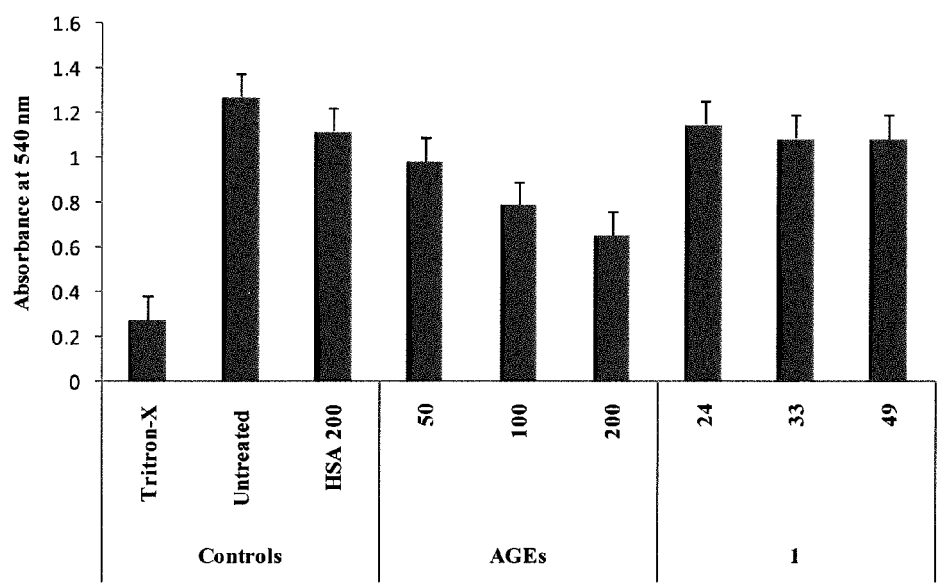
FIG. 3 depicts the effect of novel identified antiglycation agent, compound 1 on rat hepatocytes proliferation, incubated with the AGEs (200 μg/mL) The hepatocytes were treated with the specified concentrations of compound 1, for 24 hours at 37° C. The indicated optical density (Absorbance) is the mean of two independent experiments.

The presented description of the novel identified anthranilic acid derivatives and their identified mechanism of action in rat hepatocytes.

EXAMPLE 1

In-Vitro Antiglycation Activity of Novel Anthranilic Acid Derivatives Against HSA Glycation Methodology: Human serum albumin (HSA) free from essential fatty acids and rutin were obtained from Sigma Aldrich, St. Louis, Mo., USA. D-fructose, sodium azide ($NaN_3$) and dimethyl sulfoxide (DMSO) were acquired from Merck, Darmstadt, Germany. All solutions were prepared in sterile environment in deionized water at room temperature.

Assay Method: The assay was performed according the protocol of (Sattarahmady N, et al., 2007) with a little modification. Briefly, four sample solutions were prepared for the activity: (i) Negative Control; contained Human serum albumin (HSA, 10 mg/mL) in a sodium phosphate buffer ($NaHPO_4/NaH_2PO_4$, 100 mM) in a sterile environment using sodium azide ($NaN_3$, 0.1 mM) to prevent microbial growth; (ii) Glycated HSA (Control); HSA (10 mg/mL) with fructose (500 mM) was incubated in a sodium phosphate buffer (100 mM) under sterile environment containing sodium azide (0.1 mM); (iii) Positive Control; HSA (10 mg/mL) was incubated with fructose (500 mM) containing rutin (1 mM), which was used as a reference compound, since it exhibited higher antiglycation activity than aminoguanidine, previously used antiglycation agent and sodium azide (0.1 mM); and (iv) Test Sample; Test compounds (novel anthranilic acid derivatives, compounds 1-18) were dissolved in a DMSO (10%) to a final concentration of 1 mM, containing HSA (10 mg/mL), fructose (500 mM) and sodium azide (0.1 mM) in a sodium phosphate buffer. Each sample solution (200 μL, final reaction volume) in triplicate loaded a 96-wll black fluorescence plate and was incubated for a week at 37° C. in an incubator.

AGEs Detection by Fluorescence Assay: Fluorescence of glycated HSA was determined by AGEs-specific wavelength 340 nm excitation and 440 nm emission, which is an indicator of AGEs-induced degradation of protein by Spectra Max Spectrophotometer, Applied Biosystems, CA, USA.

Determination of $IC_{50}$ Values: The $IC_{50}$ values of anthranilic acid derivatives, which exhibited moderate to excellent antiglycation activity, were determined by EZ-Fit software EZ-Fit software.

Estimation of Percentage Inhibition of AGE-HSA: The following formula was used to determine the percentage inhibition of fluorescence, which is the characteristic of glycated proteins, such as AGE-HSA (Fructose-derived AGEs).

% Inhibition of flu=(1−Fluorescence of test compounds/Fluorescence of AGE-HSA)×100

Where,
Test compounds=Anthranilic acid derivatives
AGE-HSA=AGE-Modified HSA

The entire series of novel anthranilic acid derivatives were found to be active against the glycation of protein (AGE-modified Albumin). Compounds 1 and 14 exhibited the remarkable antiglycation activity with $IC_{50}$=67.2±0.004 and 84.8±0.003 μM, respectively, which is lower than the reference compound, rutin ($IC_{50}$=70±0.5 μM). While, other compounds of the series exhibited a moderate antiglycation activity against the glycation process (see Table-1).

The preliminary findings based on the limited structure-activity relationship (SAR) studies demonstrated that the $NO_2$ group on the phenyl ring in this novel class of inhibitors, novel anthranilic acid derivatives is necessary for antiglycation activity. The position of a $NO_2$ group, particularly at para-position appears to have a strong influence on the antiglycation activity. Therefore, the position and number of $NO_2$ groups on the phenyl ring affect the activity of these novel antiglycation agents, anthranilic acid derivatives.

EXAMPLE 2

Inhibition of Fructose-derived AGE-Mediated Generation of Reactive Oxygen Species (ROS) in Rat Hepatocytes by Novel Anthranilic Acid Derivatives Methodology: DCFH-DA (Dichlorofluorescin diacetate), $H_2O_2$ (Hydrogen peroxide), DMSO (Dimethyl sulfoxide) and PBS (Phosphate buffer saline) were obtained from Sigma, St. Louis, Mo., USA. 96-well black fluorescence plates (Tissue culture treated) were purchased from Thermo Fisher Scientific, Waltham, Mass., USA.

Assay Method: Briefly, rat hepatocytes (CC1-Cell line, $6 \times 10^4$ cells/mL) were loaded on a black fluorescence 96-well tissue culture treated plate for 24 hours at 37° C. in an incubator, containing 5% $CO_2$. The cells were serum starved for another 24 hours by adding serum free medium-MEM (minimum essential medium) prior to treatment with fructose-derived AGE and the test compounds, anthranilic acid derivatives. Initially the cells were treated with non fluorescent probe, DCFH-DA (10 μM) in the dark for 45 mins. Following incubation the cells were washed twice with 1×PBS and were treated with different concentrations of the AGEs, such as 0, 50, 100, and 200 μg/mL, to evaluate the AGEs influence on the generation of intracellular ROS in a concentration dependent manner. The cells were then treated with the test compounds (novel anthranilic acid derivatives) at various concentrations 24, 33, and 49 μM, co-incubated with the AGE (200 μg/mL) for 24 hours at 37° C. At the end of the incubation, just before 1 hour, the cells were incubated with $H_2O_2$ (0.5%) as a control.

Fluorescence Detection: The intensity of green fluorescence, which is emitted upon the oxidation of the probe in the presence of intracellular ROS, is measured at the excitation and emission wavelength of 490 nm and 520 nm, respectively, by Spectra Max Spectrophotometer, Applied Biosystems, CA, USA.

Estimation of Percentage Inhibition of AGE-Induced Intracellular Generation of ROS by Novel Anthranilic Acid Derivatives: The percentage inhibition of AGEs-mediated intracellular generation of ROS in rat hepatocytes in the presence or absence of novel antiglycation agent, anthranilic acid derivative, was estimated by the following formula.

% Inhibition=100−[(Fluorescence of test compound−Fluorescence of blank)/(Fluorescence of control−Fluorescence of blank)×100]

Where,
Test compound=anthranilic acid derivative
Blank=Untreated normal rat hepatocytes
Control=Hepatocytes treated with 0.5% $H_2O_2$ We observed that the intensity of green fluorescence was increased with the increasing concentration of Fru-AGEs (see Table. 2). Therefore, we selected 200 μg/mL concentration of the AGEs to determine the potential of compound 1, novel identified antiglycation agent belongs to anthranilic acid derivatives, which showed the strong inhibitory potential against HSA glycation. Previously, the AGE concentration (200 μg/mL) was identified as representative of the AGEs concentration found in the plasma of patients with diabetes and was associated with the inhibition of NO production in the endothelial cells (Han Yi, et al., 2010).

TABLE 2

| AGEs Concentration | Fluorescence (Average) |
|---|---|
| 200 μg/mL | 201.9 |
| 100 μg/mL | 135.3 |
| 50 μg/mL | 114.4 |
| HSA 200 μg/mL | 92.3 |

Inhibition of the Intracellular ROS Generation by Novel Anthranilic Acid Derivative, Compound 1 (24 μM): The rat hepatocytes (CC1-Cell line) were treated with compound 1, novel identified antiglycation agent, initially at 24 μM concentration, co-incubated with the AGE 200 μg/mL. The study was conducted to determine the antiglycation activity of the compound 1 at the cellular levels by decreasing the AGEs-induced intracellular generation of ROS, particularly hydrogen peroxide ($H_2O_2$), peroxynitrite (NOO.), and hydroxyl radical (OH.) hydrogen peroxide ($H_2O_2$), peroxynitrite (NOO.), and hydroxyl radical (OH.) via DCFH-DA technique. We observed that compound 1 reduced the intensity of green fluorescence (see Table. 3), and hence the Fru-AGE-induced intracellular generation of ROS by 93.4% at 24 μM concentration.

Inhibition of the Intracellular ROS Generation by Novel Anthranilic Acid Derivative, Compound 1 (33 μM): The novel identified antiglycation agent, compound 1 of anthranilic acid derivatives, was found equally effective at 33 μM concentration in reducing the Fru-AGE-mediated intracellular generation of ROS in rat hepatocytes, as it was at relatively lower concentration (24 μM). Compound 1 decreased the intracellular generation of ROS in response to Fru-AGE by 86.9% (see Table. 3).

TABLE 3

| Compound 1 Conc. μM | Fluorescence (Average) | Percentage Inhibition |
|---|---|---|
| 24 μM | 90.6 | 93.4% |
| 33 μM | 101.2 | 86.9% |
| 49 μM | 139.5 | 63.2% |

Inhibition of the Intracellular ROS Generation by Novel Anthranilic Acid Derivative, Compound 1 (49 μM): The novel antiglycation agent, compound 1 had shown a moderate inhibitory influence on the intracellular generation of ROS induced by Fuc-AGE (200 μg/mL) at relatively higher concentration (49 μM (see Table. 3).

The study also highlights the potential role of novel identified antiglycation agent as an antioxidant, since it prevents the hepatocytes from the intracellular oxidative stress induced by Fru-AGE. Compound 1 has the potential to compete with Fru-AGE for the RAGE (receptors for advanced glycation end products) at the receptor level. The RAGE are expressed on many cells types and their expressions are up-regulated under hyperglycemic conditions, particularly diabetes. It has been identified that AGE-RAGE interaction-mediated oxidative stress is associated with the intracellular damages and vasculopathies. Therefore, AGE-RAGE interaction is a novel therapeutic target for delaying and preventing diabetes late complications (Yamagishi S, et al., 2011). Our identified compound 1 was found to be effective in this regard and might offer potential novel therapeutic modality for the treatment of diabetic late complications.

EXAMPLE 3

Inhibition of the AGE-Mediated Reduced Growth of Rat Hepatocytes by Novel Anthranilic Acid Derivative Methodology: Normal, rat hepatocytes (CC1-Cell line) was purchased from ATCC, Manassas, Va., USA. MEM (Minimum Essential Medium) with L-glutamine, trypsin-EDTA, sodium bicarbonate and penicillin-streptomycin were obtained from Sigma, St. Louis, Mo., USA. 96-well tissue culture treated, sterile, round bottom plates were acquired from Thermo Fisher Scientific, Waltham, Mass., USA.

Assay Method: Briefly, rat hepatocytes (CC1-Cell line, $5 \times 10^4$ cells/mL) incubated in a 96-well, tissue culture treated plate, were treated initially with different concentrations of fructose-derived AGEs, such as 0, 50, 100, and 200 µg/mL, which were prepared by incubating HSA (Human serum albumin, 20 mg/mL) with fructose (500 mM) solution containing penicillin (200 U/mL), gentamycin (80 µg/mL) and streptomycin (200 µg/mL) in a sodium phosphate buffer (100 mM) for 12 weeks at 37° C. The cells were then incubated with different concentrations, such as 24, 33, and 49 µM, of test compound (novel identified antiglycation agent, anthranilic acid derivative), co-incubated with the AGEs (200 µg/mL) for 24 hours at 37° C. in an incubator containing 5% $CO_2$. All the treatment with the AGEs and the test compound were done in SFM (serum free medium), and Triton X-100 treated hepatocytes were used as a blank, while untreated normal cells were used as a control.

Determination of Cellular Proliferation: At the end of the incubation, the sample solution was removed and MTT-dye ((2 mg/mL, 50 µL) was added to each well. The final reaction volume (200 µL) was reconstituted by MEM (serum free-Minimum essential media). The plate was incubated for 4 hours at 37° C. in 5% $CO_2$ containing incubator. Following incubation, the serum free medium was removed and the crystals were dissolved by adding DMSO (100 µL) in each well.

Absorbance Detection: The absorbance of the colored solution was measured at 540 nm by Spectra Max Spectrophotometer, Applied Biosystems, CA, USA.

Estimation of Percentage Inhibition of AGE-Induced Diminished Cellular Proliferation: The percentage inhibition of AGEs-mediated diminished rat hepatocytes proliferation in the presence or absence of novel antiglycation agent, anthranilic acid derivative, was estimated by the following formula.

% Inhibition=100−[(Absorbance of test compound−Absorbance of blank)/(Absorbance of control−Absorbance of blank)×100]

Where,
Test Compound=Novel anthranilic acid derivative
Blank=Hepatocytes treated with Triton X-100
Control=Untreated normal rat hepatocytes We found that fructose-derived AGEs causes the diminished growth of rat hepatocytes, as previously reported by other investigators, and concentration dependent effects were obtained by increasing the AGE concentration (50, 100 and 200 µg/mL) (see Table. 4). Therefore, the AGEs (200 µg/mL) were used to analyze the antiglycation potential of novel compound 1 at the receptor level, particularly on the vulnerable proliferation of the hepatocytes.

TABLE 4

| AGEs Concentration | Absorbance (Average) | % Inhibition |
| --- | --- | --- |
| 200 µg/mL | 0.65 | 62.4% |
| 100 µg/mL | 0.78 | 48.6% |
| 50 µg/mL | 0.98 | 28.8% |
| HSA 200 µg/mL | 1.11 | 15.6% |

Inhibition of the AGE-mediated Inhibited Proliferation of Rat Hepatocytes by Novel Anthranilic Acid Derivative, Compound 1 (24 µM): The hepatocytes analyzed initially at lower concentration (24 µM) of compound 1, anthranilic acid derivative, by employing MTT-based cytotoxicity assay. We observed that the hepatocytes, co-incubated with the AGEs (200 µg/mL), the percentage of growth inhibition was merely 12% (see Table. 5), and hence compound 1 was found effective in reducing the toxicity of the AGEs at 24 µM concentration.

Inhibition of the AGE-mediated Inhibited Proliferation of Rat Hepatocytes by Novel Anthranilic Acid Derivative, Compound 1 (33 µM): Compound 1, anthranilic acid derivative, was found equally effective at 33 µM concentration, as we observed at 24 µM concentration, co-incubated with the AGEs (200 µg/mL). Therefore, no cytotoxic effect of the AGEs on the hepatocytes was observed (see Table. 5).

Inhibition of the AGE-mediated Inhibited Proliferation of Rat Hepatocytes by Novel Anthranilic Acid Derivative, Compound 1 (49 µM): Compound 1 belongs to anthranilic acid derivatives was also analyzed at a relatively higher concentration (49 µM) to antagonize the AGE-induced cytotoxic effect on the hepatocytes proliferation. Compound 1 was found safe and effective at such a higher concentration in reducing the toxic effects of the AGEs on the hepatocytes proliferation (see Table. 5).

TABLE 5

| Compound 1 Conc. | Absorbance (Average) | Percentage Inhibition |
| --- | --- | --- |
| 24 µM | 1.15 | 12.3% |
| 33 µM | 1.09 | 18.5% |
| 49 µM | 1.08 | 18.8% |

Compound 1 belongs to anthranilic acid derivatives, was found to be effective at various concentrations such as 24, 33 and 49 µM, co-incubated with Fru-AGE in ameliorating the AGEs-induced inhibited growth of the hepatocytes. It has been identified that AGE-RAGE interaction-mediated intracellular oxidative stress is associated with the activation of redox-sensitive transcription factor, NF-κB, which in turn activates many pro-inflammatory cytokines, such as TNF-α and pro-apoptotic transcription factors, such as FOXO1 (Alikhani M, et al., 2007; Ramasamy R, et al., 2005). The activated FOXO-1 induces apoptosis and impaired growth in many cell types (Alikhani M, et al., 2007). Our identified novel antiglycation, compound 1 suppressed the AGE-mediated toxicity of the hepatocytes, and hence prevents the hepatocytes from premature senescence and aging effects of Fru-AGEs.

What is claimed is:

1. A method of inhibiting formation of advanced glycation end products (AGEs) in a patient with diabetes by administering 2-(2,4-dinitroanilino)benzoic acid, wherein inhibition of AGEs reduces complications resulting from diabetes.

* * * * *